US006136157A

United States Patent [19]
Lindeberg et al.

[11] Patent Number: 6,136,157
[45] Date of Patent: Oct. 24, 2000

[54] METHOD FOR ORGANIC REACTIONS

[75] Inventors: Gunnar Lindeberg; Mats Larhed; Anders Hallberg, all of Uppsala, Sweden

[73] Assignee: Labwell AB, Uppsala, Sweden

[21] Appl. No.: 09/180,673

[22] PCT Filed: May 14, 1997

[86] PCT No.: PCT/SE97/00794

§ 371 Date: Nov. 24, 1998

§ 102(e) Date: Nov. 24, 1998

[87] PCT Pub. No.: WO97/43230

PCT Pub. Date: Nov. 20, 1997

[30] Foreign Application Priority Data

May 14, 1996 [SE] Sweden ................................. 9601856
Oct. 25, 1996 [SE] Sweden ................................. 9603913

[51] Int. Cl.$^7$ ...................................................... C07F 1/00
[52] U.S. Cl. .................................... 204/157.6; 204/157.69
[58] Field of Search ........................... 204/157.6, 157.69

[56] References Cited

U.S. PATENT DOCUMENTS

| | | | |
|---|---|---|---|
| 4,574,038 | 3/1986 | Wan ..................................... | 204/162 R |
| 4,933,461 | 6/1990 | Mills ....................................... | 546/239 |

OTHER PUBLICATIONS

Tetrahedron Letters, vol. 33, No. 15, 1992, no month available. Frantisek Adamek et al., "Microwave–Assisted Catalytic Addition of Halocompounds to Alkenes" pp. 2039–2042.
Synlett, vol. 8, Aug. 1993, Ajay K. Bose et al., "Simplified Rapid Hydrogenation Under Microwave Irradiation: Selective Transformations of B–Lactams1" p. 575–p. 576.
R.F. Heck, Palladium–Catalyzed Vinylation of Organic Halides, Organic Reactions, Ch. 2, 1982, 27, pp. 345–363.
Trost, B.M. and Verhoeven, T.R., Organopalladium Compounds in Organic Systhesis, Comprehensive Organometallic Chemistry; Wilkinson, G.; Stone, F.G.A.; Abel, E.W. Eds.; Pergamon Press; Oxford 1982, vol. 8, pp. 854–874.
Heck, R.F., Palladium Reagents in Organic Synthesis; Academic Press; London, 1985; pp. 276–290.
Heck, R.F. Vinyl Substitutions With Organopalladium Intermediates, Comprehensive Organic Synthesis; Trost, B.M.; Flemming, I. Eds.; Pergamon Press; Oxford 1991; vol. 4, pp. 833–863.
de Merijere, A.; Meyer, F.E.; Fine Feathers Make Fine Birds: The Heck Reaction in Modern Garb; Agnew Chem. Int. Ed. Engl. 1994, 33, pp. 2379–2411.
Cabri, W., CAndiani, I; Recent Developments and New Perspectives in the Heck Reaction; Acc. Chem. Res. 1995, 28, pp. 2–7.
Tsuji, J., Catalytic Reactions With Pd(O) and Pd(II); Paladium Reagents and Catalysts: Innovations in Organic Chemistry; John Wiley & Sons, Chichester 1995; pp. 125–149.
Daves, G.D. Jr.; Hallberg, A.; 1,2–Additions to Heteroatom–Substituted Olefins by Organopalladium Reagents; Chem. Rev. 1989,89; pp. 1433–1445.
Stille, J.K.; The Palladium–Catalyzed Cross–Coupling Reactions of Organotin Reagents With Organic Electrophiles; Angew. Chem. Int. Ed. Engl. 1986, 25, pp. 508–524.
Ritter, K.; Synthetic Transformations of Vinyl and Aryl Triflates: Synthesis 1993, pp. 735–762.
Tsuji, J., Palladium Reagents and Catalysts; Innovations in Organic Chemistry; John Wiley & Sons, Chichester 1995; pp. 228–239.
Miyaura, N.; Suzuki, A.; Palladium–Catalyzed Cross–Coupling Reactions of Organoboron Compounds; Chem Rev. 1995, vol. 95, No. 7, pp. 2457–2483.
Martin, A.R.; Yang, Y.; Palladium–Catalyzed Cross–Coupling Reactions of Organoboronic Acids With Organic Electrophiles; Acta Chemica Scandinavica vol. 47, 1993, pp. 221–230.
Frenette, R.; Friesen, R.W.; Biaryl Synthesis Via Suzuki Coupling on a Solid Support; Tetrahedron Letters, vol. 35, No. 49, 1994, pp. 9177–9180.
Backes, B.J.; Ellman, J.A.; Carbon–Carbon Bond–Forming Methods on Solid Support, Utilization of Kenner's "Safety–Catch" Linker; J. Am. Chem. Soc. 1994, vol. 116, pp. 11171–11172.
Han, Y.; Walker, S.D.; Young, R.N.; Silicon Directed ipso–Substitution of Polymer Bound Arylsilanes: Preparation of Biaryls via The Suzuki Cross–Coupling Reaction[1]; Tetrahedron Letters, vol. 37, No. 16, 1996, pp. 2703–2706.
Young, J.K.; Nelson, J.C.; Moore, J.S.; Synthesis of Sequence Specific Phenylacetylene Oligomers on an Insoluble Solid Support; J.Am. Chem. Soc. vol. 116, 1994, pp. 10841–10842.
Yu, K.L.; Deshpande, M.S.; Vyas, D.; Heck Reactions in Solid Phase Synthesis; Tetrahedron Letters, vol. 35, No. 48, 1994, pp. 8919–8922.
Hiroshige, M.; Hauske, J.R.; Zhou, P.; Formation of C–C Bond in Solid Phase Synthesis Using the Heck Reaction: Tetrahedron Letters, vol. 36, No. 26, 1995, pp. 4567–4570.
Goff D.A.; Zuckermann, R.N.; Solid–Phase Synthesis of Highly Substituted Peptoid (1(2H)–Isoquinolinones; J. Org. Chem. vol. 60, 1995, pp. 5748–5749.
Deshpande, M.S.; Formation of Carbon–Carbon Bond on Solid Support: Application of the Stille Reaction; Tetrahedron Letters, vol. 35. No. 31, 1994, pp. 5613–5614.
Forman, F.W.; Sucholeiki, I.; Solid–Phase Synthesis of Biaryls Via the Stille Reaction; J. Org. Chem., vol. 60, 1995, pp. 523–528.
Hermkens, P.H.H.; Ottenheijm, H.C.J.; Rees, D.; Tetrahedron Report No. 394; Tetrahedron, vol. 52, No. 13, 1996, pp. 4527–4554.

(List continued on next page.)

*Primary Examiner*—Kathryn Gorgos
*Assistant Examiner*—Edna Wong
*Attorney, Agent, or Firm*—Young & Thompson

[57] ABSTRACT

Organic reactions catalyzed by palladium, except Pd/C, are conducted with heating by microwave energy. The preferred inorganic reactions involved are coupling reactions in which a new carbon-carbon bond is formed. Preferred reactions are the Heck, Stille and Suzuki reaction. The method provides high yields in very short reaction times.

22 Claims, No Drawings

OTHER PUBLICATIONS

Fruchtel, J.S.; Jung, G.; Organic Chemistry on Solid Supports; Angnew. Chem. Int. Ed. Engl, vol. 35, 1996, pp. 17–42.

DeWitt, S.H.; Czarnik, A.W.; Combinatorial Organic Synthesis Using Parke–Davis's Diversomer Method; Acc. Chem. Res., vol. 29, 1996, pp. 114–122.

Armstrong, R.W.; Combs, A.P.; Tempest, P.A.; Brown, S.D.; Keating, T.A.; Multiple–Component Condensation Strategies for Combinatorial Library Synthesis; Acc. Chem. REs. vol. 29, 1996, pp. 123–131.

Ellman, J.A.; Design, Synthesis, and Evaluation of Small–Molecule Libraries; Acc. Chem. Res., vol. 29, 1996, pp. 132–143.

Gordon, E.M.; Gallop, M.A.; Patel, D.V.; Strategy and Tactics in Combinatorial Organic Synthesis. Applications to Drug Discovery; Acc. Chem. Res., vol. 29, 1996, pp. 144–154.

Thompson, L.A.; Ellman, J.A.; Synthesis and Applications of Small Molecule Libraries; Chem. Rev., vol. 96, 1996, pp. 555–600.

Lowe, G.; Combinatorial Chemistry; Chem. soc. Rev., vol. 24, 1995, pp. 309–317.

Bose, A.K.; Banik, B.K; Barakat, K.J.; Manhas, M.S.; Simplified Rapid Hydrogenation Under Microwave Irradiation: Selective Transformations of B–Lactams[1]: Synlett, Aug. 1993, pp. 575–576.

Adamek, F.; Hajek, M.; Microwave–Assisted Catalytic Addition of Halo–Compounds to Aikenes; Tetrahedron Letters, Vo. 33, No. 15, 1992, pp. 2039–2042.

Caddick, S.; Tetrahedron Report No. 381; Tetrahedron, vol. 51, No. 38, 1995, pp. 10403–10432.

Heck, R.F.; Nolley, Jr., J.P.; Palladium–Catalyzed Vinylic Hydrogen Substitutuion Reactions With Aryl, Benzyl, and Styryl Halides; J. Org. Chem., vol. 37, No. 14, 1972, pp. 2320–2322.

Patel, B.A.; Ziegler, C.B.; Cortese, N.A.; Plevyak, J.E.; Zebovitz, T.C.; Terpko, M.; Heck, R.F.; Palladium–Catalyzed Vinylic Substitution Reaction With Carboxylic Acid Derivatives; J. Org. Chem., vol. 42, No. 24, 1977 pp. 3903–3907.

Larock, R.C.; Gong, W.H.; Baker, B.E.; Improved Procedures for the Palladium–Catalyzed Intermolecular Arylation of Cyclic Alkenes; Tetrahedr Letters, vol. 30, No. 20, 1989, pp. 2603–2606.

Andersson, C.M.; Larsson, J.; Hallberg, A.J.; Chelation–Controlled, Palladium–Catalyzed Vinylic Substitution Reactions of Vinyl Esthers. 2–Arylethanal Equivalents From Aryl Halides; J. Org. Chem., vol. 55, 1990, pp. 5757–5761.

Larhed, M.; Andersson, C.–M.; Hallberg, A.; Chelation–Controlled, Palladium–Catalyzed Arylation of Vinyl Esthers; Acta Chemica Scandinavica, vol. 47, 1993, pp. 212–217.

Larhed, M.; Andersson, C.–M; Hallberg, A.; Chelation–Controlled, Palladium Catalyzed Arylation of Enol Esters With Aryl Triflates, Ligand Control of Selection for $\alpha$– $\beta$–arylation of [2–(Dimethylamino) Ethoxy]Ethene; Tetrahedron, vol. 50, No. 2, 1994, pp. 285–304.

Miyaura, N.; Yanagi, T.; Suzuki, A.; The Palladium–Catalyzed Cross–Coupli Reaction of Phenylboronic Acid With Haloarenes in the Presence of Bases; Synthetic Communications, vol. 11(7), 1981, pp. 513–519.

GRonowitz, S.;Bobosik, V.; Lawitz, K.; Palladium Catalyzed Synthesis of Unsymmetrical Bithienyls From Thiopheneboronic Acids and Halothiophenes; Chemica Scripta, vol. 23, 1984, pp. 120–122.

Farina, V.; Krishnan, B.; Marshall, D.R.; Roth, G.P.; Palladium–Catalyzed Coupling of Arylstannanes With Organic Sulfonates: A Comprehensive Study J. Org. Chem., vol. 58, No. 20, 1993, pp. 5434–5444.

Plevyak, J.E.; Dickerson, J.E.; Heck, R.F.; Selective Palladium–Catalyzed Vinylic Substitutions With Bromoiodo Aromatics; J. Org. Chem., vol. 44, No. 23, 1979, pp. 4078–4080.

Melpolder, J.B.; Heck, R.F.; A Palladium–Catalyzed Arylation of Allylic Alcohols With Aryl Halides; J. Org. Chem., vol. 41, No. 2, 1976, pp.265–272.

Cabri, W.; Candiani, I.; Bedeschi, A.; Penco. S.; Santi, R.; $\alpha$ Regio–Selectivity in Palladium–Catalyzed Arylation of Acyclic Enol Ethers; J. Org. Chem., vol. 57, pp. 1481–1486, 1992.

Cabri, W.; Candiani, I.; Bedeschi, A.; Santi, R.; Ligand–Controlled $\alpha$ Regioselectivity in Palladium–Catalyzed Arylation of Butyl Vinyl Ether; J. Org. Chem. vol. 55, 1990, pp. 3654–3655, no month available.

METHOD FOR ORGANIC REACTIONS

This is a national stage application of PCT/SE97/00794 filed May 14, 1997.

FIELD OF THE INVENTION

The present invention relates to a method for transition metal catalyzed organic reactions comprising a heating step. More precisely, the invention relates to organic reactions catalyzed with palladium, except Pd/C, under microwave energy. One type of organic reactions concerned are coupling reactions, in which new carbon-carbon bonds are formed.

BACKGROUND OF THE INVENTION

Transition metal catalyzed reactions have played a role in organic synthesis for a very long time. Twenty five years ago the first examples of the use of palladium as a catalyst for coupling reactions were disclosed. Since then enormous efforts have been devoted to extend the scope of palladium-catalyzed reactions. Among these, the Heck reaction[1], the Stille reaction[2] and the Suzuki reaction[3] probably represent the most applied and most reliable reactions considering the reactions delivering new carbon-carbon bond formation. These reactions allow the presence of a wide variety of substituents attached to the reactants and merit special attention due to the simplicity of the experimental procedures. The Heck reaction, which is a vinylic substitution reaction, is most frequently conducted with olefines and organo halides or triflates as reactants. Couplings of organotin reagents with organo halides or triflates are named Stille reactions. The related couplings of organoboronic acids and/or organoboronic esters with organo halides or triflates are named Suzuki reactions. These reactions are of utmost importance in organic synthesis and have all found use in Combinatorial Chemistry (CC), sometimes as key reactions in the creation of chemical libraries[4]. Combinatorial Chemistry is conducted either in solution or preferably on solid phase. Combinatorial Chemistry combined with High Throughput Screening (HTS) has revolutionized the Drug Discovery Programmes in the pharmaceutical industry during the last few years[5].

In Combinatorial Chemistry the reaction time factor is of importance. Rapid reactions are desired. The long reaction times often required in the palladium-catalyzed coupling reactions presented above is therefore in this respect a severe limitation. While some combinations of reactants allow fast conversions, and efficient use in Combinatorial Chemistry have been demonstrated, the majority of reactant combinations require unacceptable reaction times for completion. With regard to the palladium-catalyzed Heck, Stille or Suzuki reactions, attempted enhancement of the conversion rate by increasing the reaction temperature to over 130–150° C. most often leads to collapse of the catalytic system before a full conversion is achieved. Product decomposition is frequently observed and a mixture of undesired side products are formed.

PRIOR ART

Microwave assisted transition-metal catalyzed reactions of double bonds, including hydrogenation, catalyzed by RaNi or Pd/C,[6] and addition of chloronated hydrocarbons to double bonds, catalyzed by CuI[7] have been reported.

SUMMARY OF THE INVENTION

The present invention provides a method for palladium, except Pd/C, catalyzed organic reactions comprising a heating step performed with microwave energy.

In a preferred embodiment, the reactions are coupling reactions such as the Heck, Stille and Suzuki reactions.

Such reactions can be depicted as follows:

i) $Org^1X + H\text{-olefin} \rightarrow Org^1\text{-olefin}$
ii) $Org^1X + R^1_3Sn\text{-}Org^2 \rightarrow Org^1\text{-}Org^2$
iii) $Org^1X + R^2_2B\text{-}Org^3 \rightarrow Org^1\text{-}Org^3$ in which Org is an organic compound and $Org^1$ is aryl, heteroaryl, vinyl, acetylenyl, alkyl, allyl, benzyl, acyl, benzoyl, or mono or poly substituted aryl, heteroaryl, vinyl, acetylenyl, alkyl, allyl, benzyl, or benzoyl;

X is a halide, triflate, mesitylate, nonaflate, carbonylhalide, sulfonylhalide, perfluoroalkylsulfonate, arylphosphate, alkylphosphate, diarylarsine, diarylphosphine, diarylstibine, aryliodonium or diazonium salt;

the double bond in the H-olefin is unsubstituted or mono, di or tri substituted;

$R^1$ is alkyl, aryl, heteroaryl or mono or poly substituted alkyl, aryl or heteroaryl;

$Org^2 = Org^3$ and is aryl, heteroaryl, vinyl, acetylenyl, alkyl, allyl, benzyl or mono or poly substituted aryl, heteroaryl, vinyl, acetylenyl, alkyl, allyl, benzyl;

$R^2$ is OH, alkoxy, aryloxy or heteroaryloxy.

The reactions may be performed on a solid support, wherein $Org^1$, $Org^2$ or H-olefin are preferably attached to a solid support via a linker.

Furthermore, the present invention provides for use of palladium-catalyzed coupling reactions in combinatorial chemistry and for creation of chemical libraries.

DETAILED DESCRIPTION OF THE INVENTION

1. PALLADIUM-CATALYZED COUPLINGS IN SOLUTION

Microwave assisted methodology[8] is based on a fast heating of the reaction mixtures to high temperatures. The inventors surprisingly found that the Heck, Stille and Suzuki reactions in which labile organotransition metal intermediates play a pivotal role in the catatalytic cycle, are compatible with the extreme temperatures used in these reactions. It was found that the Heck, Stille and Suzuki reactions, after very short reaction times (2–7 minutes) when applying microwave assisted technology, allowed isolation of reaction products in high yields and also with high purity, see TABLE 1 below. The corresponding reactions performed with standard heating required hours to reach satisfactory yields according to literature, as denoted in TABLE 1. While an increase of the reaction temperature in the latter cases often provided complex reaction mixtures, the microwave assisted reactions were leading to essentially no undesired side products. Preferably the microwave energy is solely or predominantly in the form of a standing wave.

The inventors have reacted aryl iodides, aryl bromides and aryl triflates with various olefins (Heck reactions). These olefins were chosen to permit comparison of microwave-assisted reactions with conventionally heated reactions, with respect to regio- and stereoselectivity, as well as double bond isomerization. The reactions were conducted in sealed pyrex vessels and a commercially available reactor producing continuous irradiation was used. Our initial screening experments, with different solvents suggested that DMF was suitable for all reactant combinations tested. Acetonitrile, ethanol, water, DME and NMP are examples of other suitable solvents. With the exception of reaction scale, solvent and heating procedure, the reactions were performed under reaction conditions identical to the original procedures as described in the references cited, in order to enable an accurate comparison. The inventors intended to utilize microwave assisted reactions in Combinatorial Chemistry and the primary objective was minimization of the reaction times. Irradiation effects were altered to allow full conversions of the arylating agents in less than seven minutes.

Methyl acrylate was smoothly converted in 3.5 min at 60 W, to the corresponding cinnamic acid ester in a standard Heck reaction medium. The same transformation could be conducted at a lower power although a longer reaction time was required. In order to achieve a full consumption of 1-iodonaphthalene in a reaction with acrylonitrile in the same reaction time, a power of 80 W was used. While methyl acrylate provided the E isomer exclusively, the reaction with acrylonitrile produced a mixture of the E and Z isomers (E/Z=4/1) as expected from related standard reactions with this olefin. Arylation of styrene with iodobenzene delivered a terminal/internal ratio of 19/1, in accordance with the original procedure. Microwave assisted arylation of dihydrofuran according to Larock's original procedure furnished a mixture of double bond isomers. 2-Phenyl-2, 3-dihydrofuran was isolated in fair yield. A reaction time of 6 min at 30 W was needed in this case, to be compared with 24 hours at 80° C. when standard heating was employed. For studies of the regioselectivity with regard to the direction of insertion, alkyl vinyl ethers were used as substrates. Procedures have been developed that allow either electronically controlled internal arylation by application of bidentate ligands or alternatively, chelation-controlled terminal arylation. Microwave assisted arylation of butyl vinyl ether with aryl triflate provided a mixture of a-arylated vinyl ether and the corresponding acetophenone. 4-Acetyl tert. butylbenzene could be isolated in good yield after conducting the reaction in the presence of a minor amount of water. The reactions of dimethylaminoethyl vinyl ether with 2-naphthyl triflate as the substrate constitutes an example of a sluggish reaction that requires 9 hours at 60° C. to afford fair yields of coupled product. In the microwave assisted reaction, it was essential to employ a low effect, 35W, to avoid decomposition of the catalytic system. A longer reaction time, 7 min, was therefore needed. A highly regioselective arylation at the terminal carbon occurred, and equal amounts of the E and Z isomers were formed, in full agreement with the reference procedures. Allyldimethylamine and allyltrimethylsilane were both successfully arylated at the internal olefinic carbon with high regioselectivity after 5 minutes.

Suzuki coupling of phenyl boronic acid with 4-bromotoluene as well as Stille coupling of 4-acetyl phenyl triflate occurred smoothly with microwave irradiation.

Arylation of styrene with 4-bromo-1-iodobenzene delivered a terminal/internal ratio of 15/1 in accordance with the original procedure. The result from this reaction shows that the microwave irradiation provides the same selectivity, with respect to halide displacement as compared to the original reaction and substitution of the iodoatom occurs exclusively. No products derived from bromo substitution were formed, demonstrating the potential of microwave irradiation technology for combinatorial chemistry. The bromo atom remains intact and provides a handle for further consecutive palladium-catalyzed transformations.

2. PALLADIUM-CATALYZED COUPLINGS ON SOLID SUPPORT

The inventors have found that palladium-catalyzed reactions on polymer-support were compatible with the microwave assisted methodology. Preferably the microwave energy is solely or predominantly in the form of a standing wave. High yields of products with high purity were isolated after short reaction times. No or very limited decomposition of the solid phase was observed. Examples of microwave-assisted Suzuki couplings on solid phase are demonstrated in TABLE 2 below. We coupled 4-iodo and 4-bromo- benzoic acid to Rink resin[18] (TENTAGEL™ (see footnote 19), a grafted copolymer consisting of a low crosslinked polystyrene matrix on which polyethylene-glycol (PEG or POE) is grafted) and conducted the palladium-catalyzed reactions with aryl and heteroaryl boronic acids substituted with a variety of substituents. Both arylbromo and aryliodo groups on the resin are good coupling partners with organoboronic acids.

One example of a Stille coupling on solid phase and one example of a Heck coupling on solid phase are shown in TABLE 3.

Entry 15 in TABLE 2 demonstrates that the microwave technology permit selective coupling of 4-bromophenylboronic acid to aryl iodide attached to the resin. The organoiodide is more reactive and the bromo atom is not displaced. A high chemoselectivity is achieved and the bromo atom constitutes a handle for consecutive reactions.

TABLE 1

Palladium-Catalyzed Coupling Reactions in Solution under Microwave Irradiation

| entry | aryl halide or aryl triflate | olefine or organometallic | time effect | product | isolated yield[a] | conventional heating time (min) | yield (%) |
|---|---|---|---|---|---|---|---|
| 1 | 4-H₃CO-C₆H₄-I | CH₂=CH-C(O)OCH₃ | 3.50 min. 60 W, Pd(OAc)₂, DMF | methyl 4-methoxycinnamate | 70% | 300 | 68%[9] |
| 2 | 4-NC-C₆H₄-Br | CH₂=CH-C(O)OCH₃ | 3.50 min. 60 W, Pd(OAc)₂, DMF, o-(tol)₃P | methyl 4-cyanocinnamate | 94% | 120 | 70%[10] |
| 3 | C₆H₅-I | CH₂=CH-C₆H₅ | 2.50 min. 90 W, Pd(OAc)₂, DMF | stilbene | 87% | 120 | 75%[9] |
| 4 | 1-naphthyl-I | CH₂=CH-CN | 3.50 min. 80 W, Pd(OAc)₂, DMF | 1-naphthyl acrylonitrile | 90% | | |
| 5 | C₆H₅-I | 2,3-dihydrofuran | 6.00 min. 30 W, Pd(OAc)₂, Ph₃P, DMF, Bu₄NCl | 2-phenyl-2,5-dihydrofuran | 58% | 1440 | 76%[11] |

TABLE 1-continued

Palladium-Catalyzed Coupling Reactions in Solution under Microwave Irradiation

| entry | aryl halide or aryl triflate | olefine or organometallic | time effect | product | isolated yield[a] | conventional heating time (min) | yield (%) |
|---|---|---|---|---|---|---|---|
| 6 | 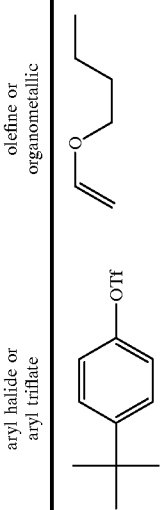 | 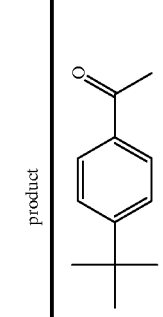 | 2.50 min, 55 W<br>Pd(OAc)$_2$, DPPP<br>DMF, H$_2$O |  | 77% | | |
| 7 | 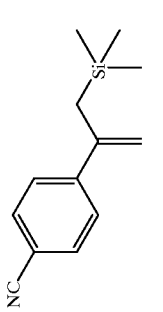 | 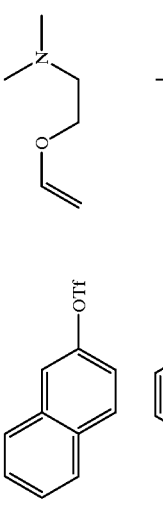 | 7.00 min, 35 W<br>Pd(OAc)$_2$, Ph$_3$P<br>DMF | 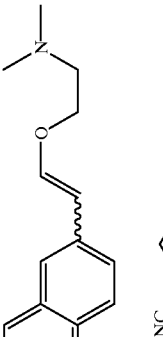 | 87% | 540 | 93%[12] |
| 8 |  | 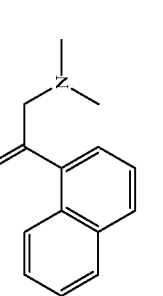 | 5.00 min, 50 W<br>Pd(OAc)$_2$, DPPF<br>CH$_3$CN | 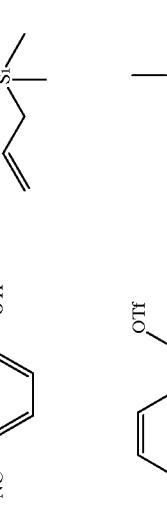 | 54% | 960 | 59% |
| 9 | 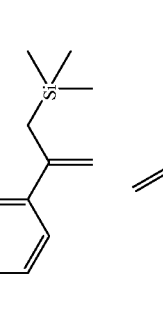 |  | 5.00 min, 50 W<br>Pd(OAc)$_2$, DPPF<br>CH$_3$CN | 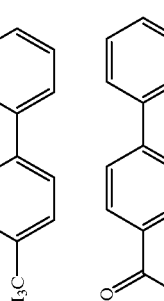 | 64% | 2880 | 72% |
| 10 | 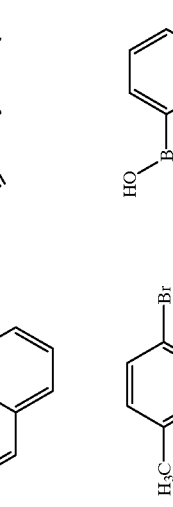 | 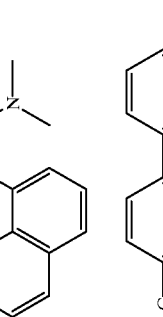 | 2.50 min, 55 W<br>Pd(PPh$_3$)$_4$, EtOH,<br>DME, H$_2$O |  | 55% | 360 | 94%[13] |
| 11 |  | 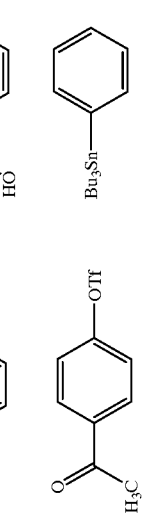 | 2.50 min, 50 W<br>Pd$_2$(dba)$_3$, Ph$_3$As,<br>LiCl, NMP | 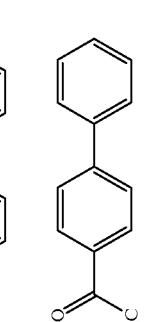 | 68% | 8400 | 82%[14] |

TABLE 1-continued
Palladium-Catalyzed Coupling Reactions in Solution under Microwave Irradiation
| entry | aryl halide or aryl triflate | olefine or organometallic | time effect | product | isolated yield[a] | conventional heating time (min) | yield (%) |
|---|---|---|---|---|---|---|---|
| 12 | 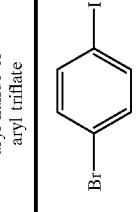 | 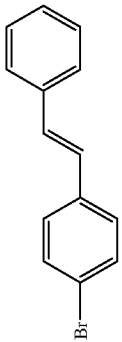 | 4,50 min, 60 W <br> $\xrightarrow{\text{Pd(OAc)}_2, \text{DMF}}$ |  | 63% | 1020 | 64%[15] |
[a]Purity > 95% by GC/MS

TABLE 2

Suzuki Coupling Reactions on Solid Phase under Microwave Irradiation[a]

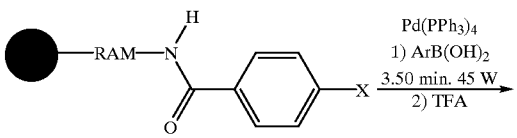

| Entry | | Entry | |
|---|---|---|---|
| 1,2 | 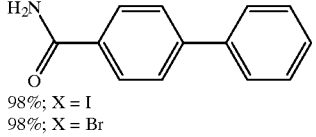 98%; X = I<br>98%; X = Br | 10 | 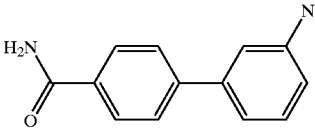 89%; X = I |
| 3,4 | 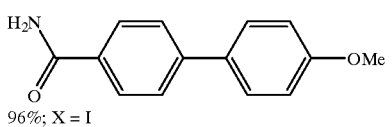 96%; X = I<br>95%; X = Br | 11,12 | 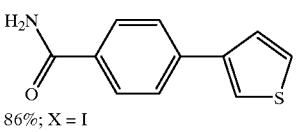 86%; X = I<br>84%; X = Br |
| 5 | 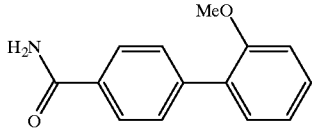 88%; X = I | 13,14 | 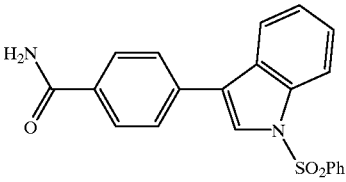 89%; X = I<br>88%; X = Br |
| 6,7 | 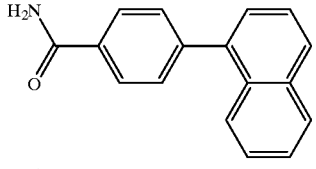 99%; X = I<br>93%; X = Br | 15[b] | 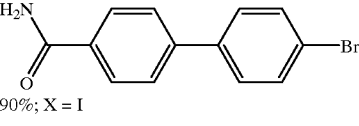 90%; X = I |
| 8,9 | 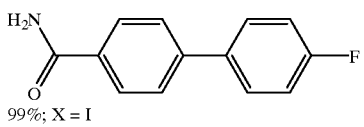 99%; X = I<br>96%; X = Br | | |

[a]Isolated yield (based upon the capacity of the Fmoc TentaGel S RAM-resin). Determined after correction (by 1H NMR) for the released PEG in the cleavage step. Purity > 95% by GC/MS.
[b]Irradiated for 6.00 min at 30 W. Purity > 80% by GC/MS.

TABLE 3

Stille and Heck Coupling Reactions on Solid Phase under Microwave Irradiation[a]

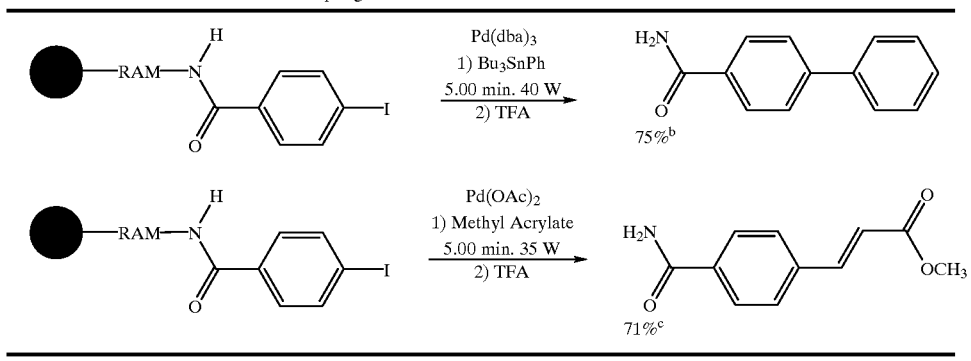

[a]Isolated yield (based upon the capacity of the Fmoc TentaGel S RAM-resin). Purity > 95% by GC/MS.
[b]The ratio of phenyl vs. butyl transfer in the isolated product was 9:1 according to $^1$H NMR.
[c]76% conversion according to GC/MS.

COMPARISON OF PRODUCT PATTERN AFTER MICROWAVE AND STANDARD HEATING.

IN SOLUTION:

The product pattern after microwave assisted palladium-catalyzed reactions and after standard heating was compared. For the reactions, entry 4 and entry 5 (see TABLE 1 above), were selected for more detailed studies. For the standard heating experiments, there was an optimal initial conversion rate of the arylhalides at 150–170° C. The reaction in entry 4, which represents the most simple system in TABLE 1, is performed with no added ligand and produces a stable product, and can be conducted at 150° C. in approximately the same reaction times as with microwave technology. A minimum amount of side products are formed with both heating techniques. The reaction in entry 5 represents a more complex system. Standard heating procedures (125–150° C.) produce here a very complex product mixture containing less than 20% of the desired product.

ON SOLID SUPPORT:

We have compared the product pattern after microwave assisted palladium-catalyzed reactions and after standard heating. Standard heating over 170° C. is not compatible with the solid support.

EXPERIMENTAL PART (E)-Methyl4-methoxycinnamate. Table 1, Entry 1. In the reaction tube were mixed 4-iodoanisole (0.234 g, 1.0 mmol), methyl acrylate (0.108 g, 1.25 mmol), palladium acetate (0.00225 g, 0.01 mmol), tri-n-butylamine (0.185 g, 1.0 mmol) and 0.50 ml DMF.under nitrogen. The contents of the flask were irradiated for 3.50 min with an effect of 60 W. After cooling, the product mixture was poured into 25 ml water and was extracted three times with 25 ml DCM. The combined extracts were washed with 25 ml water and concentrated to an oil. The crude product was purified by column chromatography on silica gel using i-hexane/diethyl ether (4/1) as the eluent. The yield was 70% (white solid).

(E)-Methyl-4-cyanocinnamate. Table 1, Entry 2. In the reaction tube were mixed 4-bromobenzonitrile (0.182 g, 1.0 mmol), methyl acrylate (0.108 g, 1.25 mmol), palladium acetate (0.00225 g, 0.01 mmol), tri-o-tolylphosphine (0.0122 g, 0.04 mmol), triethylamine (0.127 g, 1.25 mmol) and 0.50 ml DMF.under nitrogen. The contents of the flask were irradiated for 3.50 min with an effect of 60 W. After cooling, the product mixture was poured into 25 ml water and was extracted three times with 25 ml DCM. The combined extracts were washed with 25 ml water and concentrated to an oil. The crude product was purified by column chromatography on silica gel using i-hexane/diethyl ether (1/1) as the eluent. The yield was 94% (pale yellow crystals).

(E)-Stilbene. Table 1, Entry 3. In the reaction tube were mixed iodobenzene (0.204 g, 1.0 mmol), styrene (0.130 g, 1.25 mmol), palladium acetate (0.00225 g, 0.01 mmol), tri-n-butylamine (0.185 g, 1.0 mmol) and 0.50 ml DMF.under nitrogen. The contents of the flask were irradiated for 2.50 min with an effect of 90 W. After cooling, the product mixture was poured into 25 ml water and was extracted three times with 25 ml DCM. The combined extracts were washed with 25 ml water and concentrated to an oil. The crude product was purified by column chromatography on silica gel using i-hexane as the eluent. The yield was 87% (white crystals, terminal/internal arylation 19/1).

1-Naphthylacrylonitrile. Table 1, Entry 4. In the reaction tube were mixed 1-iodonaphthalene (0.254 g, 1.0 mmol), acrylonitrile (0.066 g, 1.25 mmol), palladium acetate (0.00225 g, 0.01 mmol), triethylamine (0.50 ml) and 0.50 ml DMF.under nitrogen. The contents of the flask were irradiated for 3.50 min with an effect of 80 W. After cooling, the product mixture was poured into 25 ml water and was extracted three times with 25 ml DCM. The combined extracts were washed with 25 ml water and concentrated to an oil. The crude product was purified by column chromatography on silica gel using i-hexane/diethyl ether (2/1) as the eluent. The yield was 90% (white solid, trans/cis 4/1).

2-Phenyl-2,3-dihydrofuran. Table 1, Entry 5. In the reaction tube were mixed iodobenzene (0.102 g, 0.5 mmol), dihydrofuran (0.350 g, 5.0 mmol), palladium acetate (0.00281 g, 0.0125 mmol), potassium acetate (0.147 g,1.5 mmol), n-Bu$_4$NCl (0.139 g, 0.5 mmol), triphenylphosphine (0.00328 g, 0.0125 mmol) and 1.0 ml DMF.under nitrogen. The contents of the flask were irradiated for 6.00 min with an effect of 60 W. After cooling, the product mixture was poured into 25 ml water and was extracted three times with 25 ml DCM. The combined extracts were washed with 25 ml water and concentrated to an oil. The crude product was purified by column chromatography on silica gel using pentaneldiethyl ether (19/1) as the eluent. The yield was 58% (yellow oil).

4-t-Butylacetophenone. Table 1, Entry 6. In the reaction tube were mixed 4-t-butylphenyl triflate (0.282 g, 1.0 mmol), butyl vinyl ether (0.25 g, 2.5 mmol), palladium acetate (0.00561 g, 0.025 mmol), DPPP (0.0206 g, 0.050 mmol) triethylamine (0.121 g, 1.2 mmol) 0.075 ml water and 0.75 ml DMF.under nitrogen. The contents of the flask were irradiated for 2.50 min with an effect of 55 W. After cooling, the product mixture was poured into 25 ml water and was extracted three times with 25 ml diethyl ether. The combined extracts were washed two times with 25 ml saline and concentrated to an oil. The crude product was purified by column chromatography on silica gel using i-hexane/diethyl ether (7/1) as the eluent. The yield was 77% (clear oil).

N,N-Dimethyl-2-[2-(2-naphthyl)ethenyloxy]ethanamine. Table 1, Entry 7. In the reaction tube were mixed 2-naphthyl triflate (0.276 g, 1.0 mmol), [2-(dimethylamino)ethoxy]ethene (0.23 g, 2.0 mmol), palladium acetate (0.00673 g, 0.030 mmol), triphenylphosphine (0.0173 g, 0.066 mmol) triethylamine (0.202 g, 2.0 mmol) and 0.75 ml DMF.under nitrogen. The contents of the flask were irradiated for 7.00 min with an effect of 35 W. After cooling, the product mixture was diluted with 50 ml pentane, transferred to a separatory funnel and washed with 2×25 ml water. Additional extraction of the aqueous phases was performed with 25 ml pentane. The combined organic portions were then treated 5 times with 20 ml of 0.1 M HCl. The aqueous extracts were combined, poured into a flask containing excess NaOH (1.0 M) and was extracted with 2×50 ml pentane. The combined organic phases were dried ($K_2CO_3$) and concentrated by evaporation. The yield was 87% (yellow oil, trans/cis 1/1).

2-(4-Cyanophenyl)allyltrimethylsilane. Table 1, Entry 8. In the reaction tube were mixed 4-cyanophenyl triflate (0.251 g,1.0 mmol), allyltrimethylsilane (0.571 g, 5.0 mmol), palladium acetate (0.00673 g, 0.030 mmol), DPPF (0.0366 g, 0.066 mmol), potassium carbonate (0.207 g, 1.5 mmol) and 1.0 ml acetonitrile.under nitrogen. The contents of the flask were irradiated for 5.00 min with an effect of 50 W. After cooling, the product mixture was poured into 25 ml water and was extracted three times with 25 ml diethyl ether. The combined extracts were washed two times with 25 ml saline and concentrated to an oil. The crude product was purified by repeated Kugelrohr distillation. The yield was 54% (clear oil).

2-(2-Naphthyl)N-allyidimethylamine. Table 1, Entry 9. In the reaction tube were mixed 2-naphthyl triflate (0.276 g, 1.0 mmol), N-allyidimethylamine (0.426 g, 5.0 mmol), palladium acetate (0.00673 g, 0.030 mmol), DPPF (0.0366 g, 0.066 mmol), potassium carbonate (0.207 g, 1.5 mmol) and 1.0 ml acetonitrile.under nitrogen. The contents of the flask were irradiated for 5.00 min with an effect of 50 W. After cooling, the product mixture was poured into 25 ml water and was extracted three times with 25 ml diethyl ether. The combined extracts were washed two times with 25 ml saline and concentrated to an oil. The crude product was purified by repeated Kugelrohr distillation. The yield was 64% (clear oil).

4-Methylbiphenyl. Table 1, Entry 10. In the reaction tube were mixed 4-bromotoluene (0.171 g, 1.0 mmol), phenylboronic acid (0.134 g, 1.1 mmol), Pd($PPh_3$)$_4$ (0.0347 g, 0.030 mmol), sodium cabonate (0.212 g, 2.0 mmol), 0.187 ml 95% ethanol, 0.375 ml water and 0.75 ml DME.under nitrogen. The contents of the flask were irradiated for 2.50 min with an effect of 55 W. After cooling, the product mixture was poured into 25 ml water and was extracted three times with 25 ml DCM. The combined extracts were washed with 25 ml saline and concentrated to an oil. The crude product was purified by column chromatography on silica gel using i-hexane as the eluent. The yield was 55% (white solid).

4'-Phenylacetophenone. Table 1, Entry 11. In the reaction tube were mixed 4-acetylphenyl triflate (0.268 g, 1.0 mmol), phenyltributyltin (0.441 g, 1.2 mmol), $Pd_2dba_3$ (0.00916 g, 0.010 mmol), triphenylarsine (0.0245 g, 0.080 mmol), lithium chloride (0.127 g, 3.0 mmol) and 1.0 ml NMP.under nitrogen. The contents of the flask were irradiated for 2.50 min with an effect of 50 W. After cooling, addition of 1 M aqueous KF (4 ml) with stirring for 120 min, were followed by dilution (DCM) and filtration through a pad of celite. The filtrate was washed with water (25 ml). Additional extraction of the aqueous phase was performed with DCM (2×25 ml). The combined extracts were washed with 25 ml saline and concentrated to an oil. The crude product was purified by column chromatography on silica gel using i-hexane/ethyl acetate (10/1) as the eluent. The yield was 68% (white solid).

(E)4-Bromostilbene. Table 1, Entry 12. In the reaction tube were mixed 4-bromoiodobenzene (0.283 g, 1.0 mmol), styrene (0.115 g, 1.1 mmol), palladium acetate (0.00225 g, 0.01 mmol), triethylamine (0.111 g, 1.1 mmol) and 0.50 ml DMF.under nitrogen. The contents of the flask were irradiated for 4.50 min with an effect of 60 W. After cooling, the product mixture was poured into 25 ml water and was extracted three times with 25 ml DCM. The combined extracts were washed with 25 ml water and concentrated to an oil. The crude product was purified by column chromatography on silica gel using i-hexane as the eluent. The yield was 63% (white crystals).

General procedure for Suzuki coupling reactions on solid phase. Table 2. A sealed Pyrex tube was charged, under nitrogen, with 4-iodo or 4-bromo functionalised resin (100 mg, loading ~0.23 mmol/g), Pd($PPh_3$)$_4$ (1.15 mg, 0.0010 mmol), aryl boronic acid (0.20 mmol), 2M $Na_2CO_3$ (0.10 ml, 0.20 mmol), $H_2O$ (0.30 ml), ethanol (0.19 ml) and DME (0.75 ml). After irradiation, the mixture was cooled to room temperature. The resin was transferred thereafter to a 3-ml disposable syringe equipped with a porous polyethylene filter using $H_2O$/DME, washed with successive portions of $H_2O$, DME, DMF, sat. KCN/DMSO, MeOH, $H_2O$, MeOH and DCM (2×3 ml each) and dried. The resin was treated with 99% aq. TFA for 1 h, filtered and washed with 0.5 ml TFA and 2×0.5 ml DCM. The filtrates were combined and evaporated to dryness to yield the biaryl. All products gave satisfactory $^1$H NMR spectra as well as appropriate ion identification by mass spectrometry (El or PDMS) and had purity >95% by GC/MS.

Procedure for the Stille coupling reaction on solid phase. Table 3. 4-Iodo functionaiised resin (100 mg, loading ~0.23 mmol/g), $Pd_2dba_3$ (1.05 mg, 0.00115 mmol), $AsPh_3$ (1.41 mg, 0.0046 mmol), phenyltributyltin (73.4 mg, 0.20 mmol) and dry NMP (1.0 ml) were placed in a Pyrex tube under nitrogen. The tube was closed, placed in the microwave cavity and irradiated for 5.00 min. at 40 W. After cooling, the product was washed and cleaved from the resin as described for the Suzuki coupling reactions. The ratio of phenyl vs. butyl transfer in the isolated product was 9:1 according to $^1$H-NMR (75% yield, white solid).

Procedure for the Heck coupling reaction on solid phase. Table 3. 4-Iodo functionalised resin (50 mg, loading ~0.23 mmol/g), methyl acrylate (0.046 g, 0.53 mmol), palladium acetate (0.00074 g, 0.0033 mmol), tri-o-tolylphosphine (0.00322 g, 0.0106 mmol), triethylamine (0.011 g, 0.11 mmol) and 1.0 ml DMF were placed in a Pyrex tube under nitrogen. The tube was closed, placed in the microwave cavity and irradiated for 5.00 min. at 35 W. After cooling, the product was washed and cleaved from the resin as described for the Suzuki coupling reactions. The crude product was purified by column chromatography on silica gel using i-hexane/DCM (1/1) as the eluent. The yield was 71% (white solid).

In the Heck, Suzuki and Stille reactions performed with microwave energy according to the invention catalytic systems commonly used in these reactions are employed. Below a listing of suitable catalytic systems of soluble palladium complexes will follow. The listed catalytic systems are not the active catalysts in the reactions but rather precatalysts generating the active catalyst.

$Pd(O)(PPh_3)_4$ $Pd(II)Cl_2(PPh_3)_2$ $Pd(II)OAc_2$+ligand (eg. $PPh_3$, $AsPh_3$, tri(2-furyl)phosphine, tri (o-tolyl) phosphine, DPPF (1,1'-bis (diphenylphosphino)ferrocene or BINAP (2,2'-bis (diphenylphosphino)-1,1'-binaphtyl)

$Pd(O)_2(dba)_3$—$CHCl_3$ or $Pd(O)(dba)_2$+ligand as above

Often additions are made to the catalytic systems, such as LiCl, $Bu_4NCl$, Cu salts, Ag salts, or Tl salts.

Furthermore, it is to be understood that the microwave energy used in the method according to the present invention can be generated in different ways. The microwaves should be generated in a controlled and most of all reproducible way. For large volumes (>0.2 mL), this can be achieved by using magnetrons or clystrons. For small reaction volumes (approx. 100 $\mu$l) semiconductor generated microwaves are preferably used.

The standing wave, single mode, performance of the applied microwaves makes it possible to focus and optimise the coupling of the microwaves to the reaction samples in a highly reproducible way.

REFERENCES AND NOTES

1. For reviews on the Heck reaction see;
    a) Heck, R. F. *Org React.* 1982, 27, 345,
    b) Trost, B. M. and Verhoeven, T. R. *Comprehensive Organometallic Chemistry*; Wilkinson, G.; Stone, F. G. A.; Abel, E. W. Eds.; Pergamon Press: Oxford 1982; vol 8, pp. 854,
    c) Heck, R. F. *Palladium Reagents in Organic Synthesis*; Academic Press; London. 1985; pp 276,
    d) Heck, R. F. *Comprehensive Organic Synthesis*; Trost, B. M.; Flemming, I. Eds.; Pergamon Press: Oxford 1991; vol. 4, pp. 833,
    e) de Meijere, A.; Meyer, F. E. *Angew. Chem. Int. Ed. Engl.* 1994, 33, 2379,
    f) Cabri, W.; Candiani, I. *Acc. Chem. Res.* 1995, 28, 2,
    g) Tsuji, J. *Palladium Reagents and Catalysts: Innovations in Organic Chemistry*, John Wiley & Sons, Chichester 1995; pp. 125. For Heck arylation of heteroatom-substituted double bonds see;
    h) Daves, G. D. Jr.; Hallberg, A. *Chem. Rev.* 1989, 89, 1433.
2. For reviews on the Stille reaction see: a) Stille, J. K. *Angew. Chem. Int. Ed. Engl.* 1986, 25, 508, b)Ritter, K. *Synthesis* 1993, 735,.c) Tsuji, J. *Palladium Reagents and Catalysts: Innovations in Organic Chemistry*; John Wiley & Sons, Chichester 1995; pp. 228.
3. For reviews on the Suzuki reaction see:
    a) Miyaura, N.; Suzuki, A. *Chem. Rev.* 1995, 95, 2457,
    b) Martin, A. R.; Yang, Y. *Acta Chem. Scand.* 1993, 47, 221.
4. Examples of Suzuki couplings in Combinatorial Chemistry:
    a) Frenette, R.; Friesen, R. W. *Tetrahedron Left.* 1994, 35, 9177,
    b) Backes, B. J.; Ellman, J. A. *J. Am. Chem. Soc.* 1994, 116, 11171,
    c) Han, Y.; Walker, S. D.; Young, R. N. *Tetrahedron Left.* 1996, 37, 2703.
    Examples of Heck couplings in Combinatorial Chemistry:
    d) Young, J. K.; Nelson, J. C.; Moore, J. S. *J. Am. Chem. Soc.* 1994, 116, 10841,
    e) Yu, K. L.; Deshpande, M. S.; Vyas, D. *Tetrahedron Left.* 1994, 35, 8919,
    f) Hiroshige, M.; Hauske, J. R.; Zhou, P. *Tetrahedron Left.* 1995, 36, 4567,
    g) Goff, D. A.; Zuckermann, R. N. *J. Org. Chem.* 1995, 60, 5748.
    Examples of Stille reactions on support-bound aryl halides:
    h) Deshpande, M. S. *Tetrahedron Left.* 1994, 35, 5613,
    i) Forman, F. W.; Sucholeiki, I. *J. Org. Chem.* 1995, 60, 523.
5. For recent reviews, see:
    a) Hermkens, P. H. H.; Ottenheijm, H. C. J.; Rees, D. *Tetrahedron* 1996, 52, 4527,
    b) Früchtel, J. S.; Jung, G. *Angew. Chem. Int. Ed. Engl.* 1996, 35, 17,
    c) DeWitt, S. H.; Czarnik, A. W. *Acc. Chem. Res.* 1996, 29, 114,
    d) Armstrong, R. W.; Combs, A. P.; Tempest, P. A.; Brown, S. D.; Keating, T. A. ibid. 1996, 29, 123,
    e) Eliman, J. A. ibid. 1996, 29, 132,
    f) Gordon, E. M.; Gallop, M. A.; Patel, D. V. ibid. 1996, 29,144,
    g) Thompson, L. A.; Ellman, J. A. *Chem. Rev.* 1996, 96, 555, h) Lowe, G. *Chem. Soc. Rev.* 1995, 24, 309.
6. Bose, A. K; Banik, B. K.; Barakat, K. J.; Manhas, M. S.; *Synlett.*, 1993, 575.
7. Adamek, F.; Hajek, M. *Tetrahedron Left.* 1992, 33, 2039.
8. Caddick, S. *Tetrahedron* 1995, 51, 10403.
9. Heck, R. F.; Nolley, Jr., J. P. *J. Org. Chem.* 1972, 37, 2320.
10. Patel, B. A.; Ziegler, C. B.; Cortese, N. A.; Plevyak, J. E.; Zebovitz, T. C.; Terpko, M.; Heck, R. F. *J. Org. Chem.* 1977, 42, 3903.
11. Larock, R. C.; Gong, W. H.; Baker, B. E. *Tetrahedron Left.* 1989, 30, 2603.
12. a) Andersson, C.-M.; Larsson, J.; Hallberg, A. *J. Org. Chem.* 1990, 55, 5757,
    b) Larhed, M.; Andersson, C.-M.; Hallberg, A. *Acta. Chem. Scand.* 1993, 47, 212,
    c) Larhed, M.; Andersson, C.-M.; Hatlberg, A. *Tetrahedron* 1994, 50, 285.
13. a) Miyaura, N.; Yanagi, T.; Suzuki, A. *Synth.Commun.*, 1981, 11, 513,
    b) DME was introduced as solvent in the Suzuki reaction by Gronowitz. Gronowitz, S.; Bobosik, V.; Lawitz, K. *Chem. Scr.* 1984, 23, 120.
14. Farina, V.; Krishnan, B.; Marshall, D. R.; Roth, G. P. *J. Org. Chem.* 1993, 58, 5434.
15. Plevyak, J. E.; Dickerson, J. E.; Heck, R. F. *J. Org. Chem.* 1979, 44, 4078.
16. Melpolder, J. B.; Heck, R. F. *J. Org. Chem.* 1976, 41, 265.
17. a) Cabri, W.; Candiani, I.; Bedeschi, A.; Penco, S.; Santi, R. *J. Org. Chem.* 1992, 57, 1481, b) Cabri, W.; Candiani, I.; Bedeschi, A.; Santi, R. *J. Org. Chem.* 1990, 55, 3654.

18. The 4-halobenzoic acids (4 eq.) were coupled to deprotected resin using 2-(1H-benzotriazole-1-yl)-1,1,3,3-tetramethyl-uronium hexafluorophosphate (HBTU, 4 eq.) and DIEA (8 eq.) for 2 h. Remaining amino groups were then capped by acetylation 19. 90 mm Fmoc TentaGel S RAM-resin (S30 023, 0.23 mmol/g capacity) purchased from Rapp Polymere.

What is claimed is:

1. A method for generating palladium-catalyzed organic reaction products, comprising performing an organic reaction catalyzed with palladium except Pd/C, the organic reaction being i) Heck reactions in which a first organic species, $Org^1X$, is reacted with a second organic species, H-Olefin, in order to provide a product, $Org^1$-Olefin, ii) Stille reactions in which a first organic species, $Org^1X$, is reacted with a second organic species, $R^1{}_3Sn\text{-}Org^2$, in order to provide a product, $Org^1\text{-}Org^2$, or iii) Suzuki reactions in which a first organic species, $Org^1X$, is reacted with a second organic species, $R^2{}_2B\text{-}Org^3$, in order to provide a product, $Org^1\text{-}Org^3$, wherein:
    $Org^1$ is aryl, heteroaryl, vinyl, acetylenyl, alkyl, allyl, benzyl, acyl, or benzoyl, or mono- or poly-substituted aryl, heteroaryl, vinyl, acetylenyl, alkyl, allyl, or benzoyl;
    X is a halide, triflate, mesitylate, nonaflate, carbonylhalide, sulfonylhalide, perfluoroalkylsulfonate, arylphosphate, alkylphosphate, diarylarsine, diarylphosphine, diarylstibine, aryliodonium salt or diazonium salt;
    H-Olefin is an olefin having a double bond and an olefinic hydrogen atom, the double bond in the H-Olefin being unsubstituted or mono-, di- or tri-substituted;
    $R^1$ is alkyl, aryl or heteroaryl, or mono- or poly-substituted alkyl, aryl or heteroaryl;
    $Org^2$ and $Org^3$ are both aryl, heteroaryl, vinyl, acetylenyl, alkyl, allyl or benzyl, or mono- or poly-substituted aryl, heteroaryl, vinyl, acetylenyl, alkyl, allyl or benzoyl; and
    $R^2$ is hydroxy, alkoxy, aryloxy or heteroaryloxy;
    wherein microwave energy is supplied to the organic reaction in order to heat said organic reaction.

2. A method according to claim 1, wherein the organic reaction is the Heck reaction.

3. A method according to claim 2, wherein the organic reaction is performed in solution.

4. A method according to claim 2, wherein the organic reaction is performed on a solid support.

5. A method according to claim 4, wherein the first organic species, $Org^1$, or the second organic species, H-Olefin, is attached to the solid support.

6. A method according to claim 5, wherein the first organic species, $Org^1$, or the second organic species, H-Olefin, is attached to the solid support via a linker.

7. A method according to claim 2, wherein the organic reaction is part of a combinatorial chemistry process.

8. A method according to claim 1, wherein the organic reaction is the Stille reaction.

9. A method according to claim 8, wherein the organic reaction is performed in solution.

10. A method according to claim 8, wherein the organic reaction is performed on a solid support.

11. A method according to claim 10, wherein the first organic species, $Org^1$, or the second organic species, $Org^2$, is attached to the solid support.

12. A method according to claim 11, wherein the first organic species, $Org^1$, or the second organic species, $Org^2$, is attached to the solid support via a linker.

13. A method according to claim 8, wherein the organic reaction is part of a combinatorial chemistry process.

14. A method according to claim 1, wherein the organic reaction is the Suzuki reaction.

15. A method according to claim 14, wherein the organic reaction is performed in solution.

16. A method according to claim 14, wherein the organic reaction is performed on a solid support.

17. A method according to claim 15, wherein the first organic species, $Org^1$, is attached to the solid support.

18. A method according to claim 17, wherein the first organic species, $Org^1$, is attached to the solid support via a linker.

19. A method according to claim 14, wherein the organic reaction is part of a combinatorial chemistry process.

20. A method according to claim 1, wherein the microwave energy is solely or predominantly provided in the form of a standing wave.

21. A method according to claim 1, wherein the organic reaction is used in the creation of a chemical library.

22. A method according to claim 1, wherein the microwave energy is provided for a period of 2–7 minutes.

* * * * *